US010188809B2

(12) United States Patent
Lee et al.

(10) Patent No.: US 10,188,809 B2
(45) Date of Patent: Jan. 29, 2019

(54) THERAPY-SPECIFIC MEDICAL PUMP

(71) Applicant: Zyno Medical, LLC., Natick, MA (US)

(72) Inventors: Chaoyoung Lee, Weston, MA (US); Mei Zhang, Sharon, MA (US)

(73) Assignee: Zyno Medical, LLC, Natick, MA (US)

( * ) Notice: Subject to any disclaimer, the term of this patent is extended or adjusted under 35 U.S.C. 154(b) by 236 days.

(21) Appl. No.: 14/678,110

(22) Filed: Apr. 3, 2015

(65) Prior Publication Data
US 2016/0287780 A1 Oct. 6, 2016

(51) Int. Cl.
G06F 19/00 (2018.01)
A61M 5/50 (2006.01)
A61M 5/172 (2006.01)
A61M 5/142 (2006.01)
A61M 5/168 (2006.01)
G16H 40/63 (2018.01)

(52) U.S. Cl.
CPC ...... *A61M 5/5086* (2013.01); *A61M 5/14216* (2013.01); *A61M 5/16827* (2013.01); *A61M 5/172* (2013.01); *G06F 19/00* (2013.01); *G06F 19/3481* (2013.01); *G16H 40/63* (2018.01); *A61M 2005/14208* (2013.01); *A61M 2205/502* (2013.01); *A61M 2205/507* (2013.01); *A61M 2205/52* (2013.01); *A61M 2205/6009* (2013.01)

(58) Field of Classification Search
CPC .. A61M 5/142; A61M 5/172; A61M 5/16827; A61M 5/14216; A61M 2205/6009; A61M 2205/52; A61M 2205/507; A61M 2005/14208; A61M 5/5086; G06F 19/3481; G06F 19/3406
See application file for complete search history.

(56) References Cited

U.S. PATENT DOCUMENTS

| 5,171,301 | A | * | 12/1992 | Vanderveen | A61M 5/168 604/141 |
|---|---|---|---|---|---|
| 8,945,043 | B2 | | 2/2015 | Lee et al. | |
| 2005/0115561 | A1 | * | 6/2005 | Stahmann | A61B 5/0031 128/200.24 |
| 2006/0047538 | A1 | * | 3/2006 | Condurso | G06F 19/326 705/3 |
| 2008/0306353 | A1 | * | 12/2008 | Douglas | G06F 19/3406 600/301 |
| 2009/0006061 | A1 | * | 1/2009 | Thukral | G06F 19/325 703/11 |
| 2012/0232520 | A1 | * | 9/2012 | Sloan | A61B 5/14532 604/504 |
| 2012/0253269 | A1 | * | 10/2012 | Patrick | A61B 8/00 604/35 |
| 2013/0144206 | A1 | | 6/2013 | Lee et al. | |
| 2014/0114238 | A1 | | 4/2014 | Lee et al. | |
| 2014/0171868 | A1 | | 6/2014 | Zhang et al. | |
| 2014/0171869 | A1 | | 6/2014 | Zhang | |
| 2014/0194717 | A1 | | 7/2014 | Lee et al. | |

(Continued)

Primary Examiner — Michael D Masinick
(74) Attorney, Agent, or Firm — Boyle Fredrickson S.C.

(57) ABSTRACT

A medical pump provides programming to assist a patient in complying with treatment schedules involving varying dosages of medicament(s). The pump includes stored treatment schedules and protocols that describe control of flow control device(s) for delivering different medicines according to the protocols and which may provide reminders and instructions to the patient.

15 Claims, 4 Drawing Sheets

(56) References Cited

U.S. PATENT DOCUMENTS

| | | | | |
|---|---|---|---|---|
| 2015/0157791 A1* | 6/2015 | Desch | .................... | G16H 10/65 |
| | | | | 604/506 |
| 2016/0012205 A1* | 1/2016 | Saint | ................. | A61M 5/31528 |
| | | | | 604/154 |
| 2016/0224736 A1* | 8/2016 | Patel | .................... | G06F 19/322 |

* cited by examiner

THERAPY-SPECIFIC MEDICAL PUMP

BACKGROUND OF THE INVENTION

The present invention relates to medical pumps tailored for implementation of a specific therapy.

Medical pumps, such as syringe pumps or peristaltic infusion pumps, are known for computer-controlled delivery of medication or contrast agents (henceforth medicaments) to patients over a period of time. Typically the medicament is delivered in a syringe (for a syringe pump) or a flexible bag (for a peristaltic infusion pump, or ambulatory pump) that may be connected to an IV line and attached to a needle inserted into the patient. When a nurse or other healthcare professional ministering to the patient receives the medicament, the healthcare professional reviews the medicament description for correctness and enters the desired dose and rate into the pump. Other pump parameters such as alarm limits and the like may also be programmed at this time. The syringe or IV line must then be mechanically connected to the pump mechanism, the needle introduced into the patient, and the mechanism activated to begin pumping.

Advances in medical equipment design have greatly simplified the operation of such pumps permitting them to be used in a wide variety of environments and by different operators including not only trained healthcare professionals in a hospital environment but also in a home care setting by a visiting nurse or even by the patients themselves. U.S. patent application Ser. No. 13/488,841 filed Jun. 5, 2012, and U.S. patent application Ser. No. 13/190,312 filed Feb. 26, 2014, assigned to the assignee of the present application and hereby incorporated by reference, describe systems that providing features that assist patients in operating pumps with minimal supervision including allowing the pump to be preprogrammed by a pharmacist and/or skilled healthcare professional and providing certain on-site checks, for example, of proper medicament.

The treatment of some medical conditions can require the administration of multiple drugs in a particular sequence according to a complex schedule that varies over time. For example, in the treatment of Primary Immunodeficiency (PI), a primary medicament of therapeutic immune globulin containing IgG antibodies must be administered only after a preliminary medicament of Recombinant Human Hyaluronidase is injected. This latter preliminary drug modifies dermal tissue to better disburse the antibodies of the primary drug.

Each treatment session requires the administration of both drugs in the particular order and the entire treatment requires adhering to a schedule with changing dosages over time. Ideally, these treatments are self-administered by the patient, but the complexity of the treatment process can be difficult for some patients to properly manage.

SUMMARY OF THE INVENTION

The present invention provides a medical pump that can be linked to a specific medical therapy, for example, to implement multiple therapeutic steps with different drugs over an extended schedule. The pump is programmable with a multi-day schedule, and includes protocols to deliver a sequence of drugs at each scheduled session in different dosages with guidance to the patient.

In one embodiment, the invention provides a programmable medical pump having a housing holding at least one metering device for metering a flow of liquid medicament. The metering device being controlled by an electronic computer accessing an electronic memory holding a multi-session treatment schedule describing different treatment sessions and treatment protocols for a delivery of liquid medicament through the first and second metering device for each session. The electronic computer executes a stored program to: (1) identify a current session of the treatment schedule; (2) determine a treatment protocol for a current session; and (3) execute a protocol providing sequential delivery of medicament through the first and second metering device for the current session.

It is thus a feature of at least one embodiment of the invention to enlist capabilities of a medical pump not simply for the delivery of medicaments but also in managing and scheduling complex multidrug therapies.

The pump may include a user interface so that the computer may provide instructions via the user interface relative to the protocol to the patient from at least one of the treatment sessions and protocols.

It is thus a feature of at least one embodiment of the invention to use the pump to deliver timely step-by-step instructions to the patient to guide the patient through complex medical therapies coordinated with the functions of the pump.

The programmable medical pump may further provide reminders to the patient of the current session, for example, by means of a text display, and image display or audio transducer.

It is thus a feature of at least one embodiment of the invention to make use of an internal calendar system and multisession schedule of the pump to help enforce patient compliance with complex regimes.

The current session may identify a first and second medicament for the protocol and the pump may provide a code sensor for reading encoded information on medicament containers to confirm proper medicament for use with the current session.

It is thus a feature of at least one embodiment of the invention to assist the patient in ensuring that proper medicaments are employed for a given session both in terms of medicament type, and dose where different doses are available in different containers.

The code sensor may be a near field communication sensor.

It is thus a feature of at least one embodiment of the invention to provide a confirmation mechanism that may be integrated in the patient's collection of therapy materials for a session where the patient scans immediately available medicament containers.

The first flow control device may be a syringe pump for receiving and activating a syringe and the second flow control device may be a peristaltic pump for pumping liquid through an IV tube attached to a medicament container.

It is thus a feature of at least one embodiment of the invention to provide a system for assisting a patient in therapies that require both relatively large and small volumes of medicament that allow the patient to load the pump and then be guided through the entire process including delivery sequences and flow rates.

The programmable medical pump may include a wireless interface for communicating with a remote electronic device, and the electronic computer may communicate with the wireless interface to receive data related to one of the multi-session treatment schedule and the treatment protocols.

It is thus a feature of at least one embodiment of the invention to allow ready adjustment of the pump therapy protocol remotely, for example, to adjust doses or treatments mid-way through a therapy or between different therapies.

The electronic computer further communicates with the wireless interface to report successful completion of each session.

It is thus a feature of at least one embodiment of the invention to permit a tracking of patient compliance to better guide healthcare professionals in assisting the patient in the therapy.

The programmable medical pump may include a start pushbutton for receiving input from the patient.

It is thus a feature of at least one embodiment of the invention to provide a simple and intuitive method for the patient to signal that they have completed patient-components of the protocol as guided by the pump.

The treatment protocols may include amounts of medicine delivery for different sessions.

It is thus a feature of at least one embodiment of the invention to provide a pump system that can provide for complex variations in medicine dosage over time, for example, in acclimating a patient to a particular drug.

The treatment protocols may include a sequence of medicament deliveries using the first and second flow control devices.

It is thus a feature of at least one embodiment of the invention to assist the patient in therapies that require both the sequencing and controlling of the delivery of different drugs.

The treatment protocols may provide treatment ranges that may be modified by the patient during treatment.

It is thus a feature of at least one embodiment of the invention to permit patient control of the process within established guidelines.

The programmable medical pump may include a code sensor for reading encoded information on an identification device assessable by the patient to confirm the proper patient for the treatment sessions.

It is thus a feature of at least one embodiment of the invention to reduce the possibility of patient mis-identification when the treatment pumps are distributed to different patients by a central service or the like.

The multi-session treatment schedule may span multiple days and the electronic computer implements a calendar to identify a particular session based on a calendar day of the session.

It is thus a feature of at least one embodiment of the invention to assist patients in adhering to complex multi-day treatment by employing an essential element of those treatments in the pump.

These particular objects and advantages may apply to only some embodiments falling within the claims and thus do not define the scope of the invention.

DETAILED DESCRIPTION OF THE PREFERRED EMBODIMENT

Figure 1:
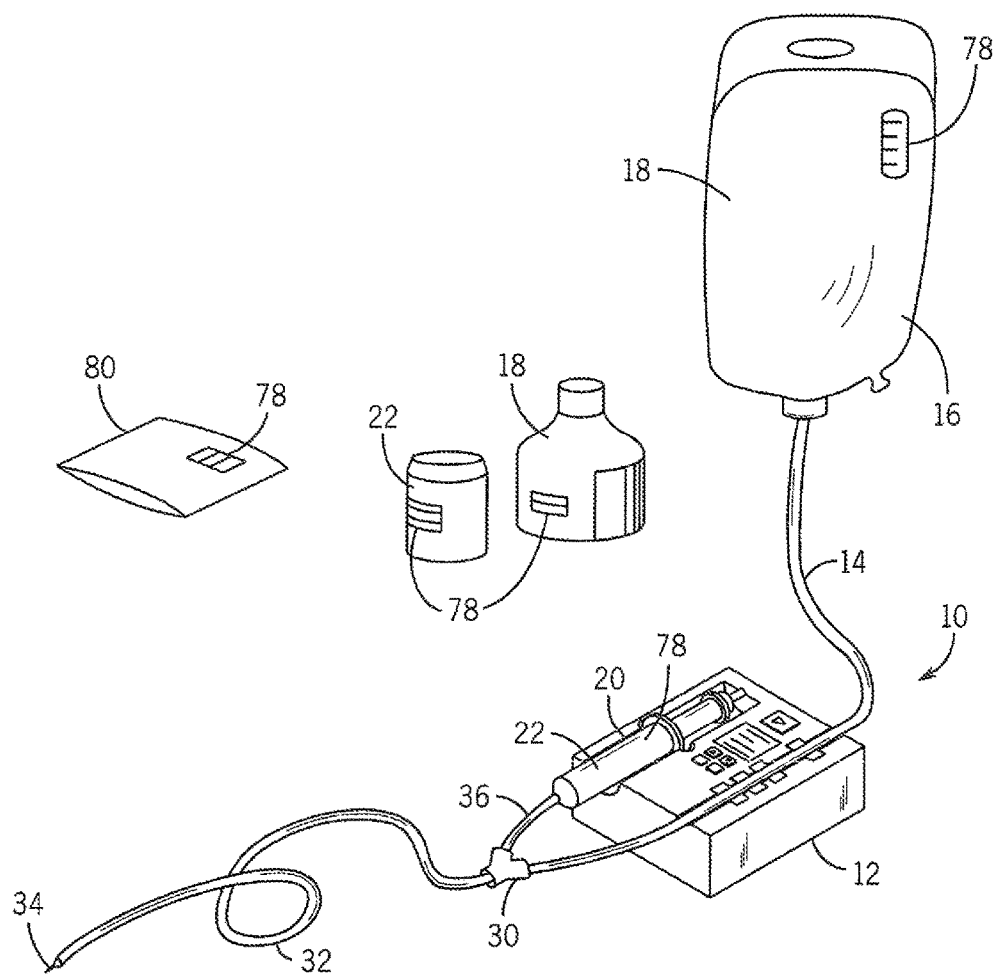
FIG. 1 is a schematic representation of a pump of one embodiment of the present invention used with dual medicaments contained in a pooling bag and a syringe and showing an IV kit for delivery of these medicaments through a needle.
Figure 2:
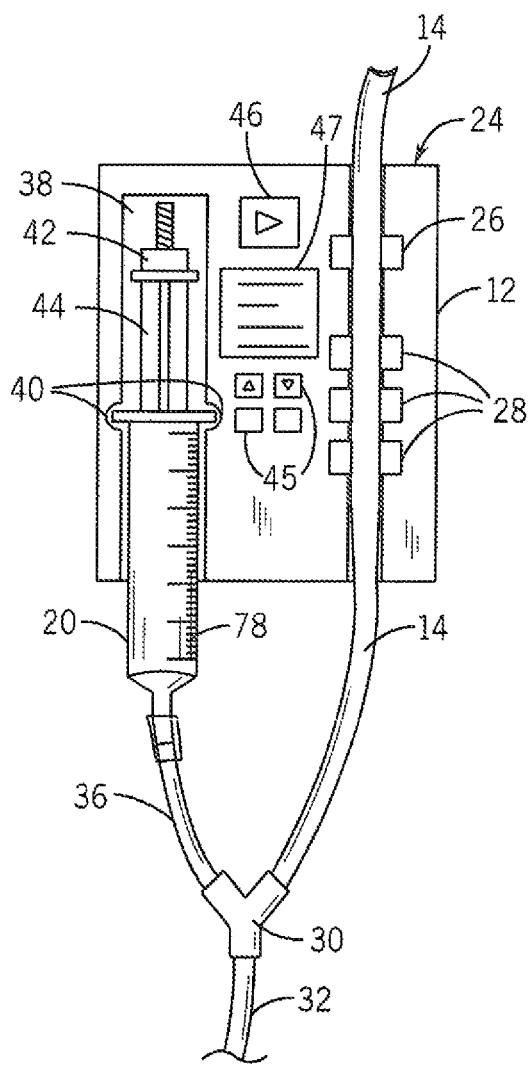
FIG. 2 is a top view of the pump of FIG. 1 showing the positioning of a syringe and an IV tube in the pump for use and showing a simplified control system providing a start button and an LCD alphanumeric display.

Referring now to FIGS. 1 and 2, a medical pump 10 of the present invention, tailored to a particular therapy, may provide for a housing 12 open on an upper surface to receive an IV line 14 and a syringe 20. The IV line 14 may receive a first medicament 18 from a medicament pooling bag 16 and the syringe 20 may hold a second medicament 22.

The IV line 14 is received within the medical pump 10 along a channel 24 extending from a top to a bottom surface of the housing 12 where it passes through IV clamp elements 26 and reciprocating actuators 28 of a peristaltic pump element. The IV clamp elements 26 may be open or closed to pass or block medicament 18 from passing through the IV line 14. Sequential action of the reciprocating actuators 28, in contrast, provides a metered pumping of the medicament 18 through the IV line 14.

After passing through the reciprocating actuators 28, the IV line 14 exits the housing 12 and joins to a Y connector 30 which leads to a common patient line 32 terminating at a needle 34 that may be inserted by the patient percutaneously at a treatment site.

A remaining branch of the Y connector 30 accepts a tubing stub 36 passing between the Y connector 30 and an outlet of the syringe 20. The body of the syringe 20 fits in a corresponding pocket 38 in the upper surface of the housing 12 which includes axially restraining grooves 40 that receive and grip an upper flange of the outer syringe body restraining the syringe 20 from axial movement.

A motorized drive arm 42 extends upward into the pocket 38 to contact an upper end of a syringe plunger 44 of the syringe 20 so that the syringe plunger 44 may be depressed into the syringe body by activation of the motorized drive arm 42 by a motor (shown in FIG. 4) beneath the upper surface of the housing 12 to provide a controlled pumping of medicament 22 from the syringe 20.

The upper face of the housing 12 may also provide a user-interface display 47, for example, an LCD display, that may display text messages and images to provide instructions and feedback to the patient as will be discussed below. A simplified user-interface input is also provided on the upper face of the housing 12 including, for example, a start button 46 for stepping through therapy stages as well as other simplified control buttons 45 (for example, increase and decrease buttons) each permitting a degree of control by the patient of the process, for example, initiating protocol, pausing the protocol, moving through protocol steps, changing flow rates and the like.

Figure 3:
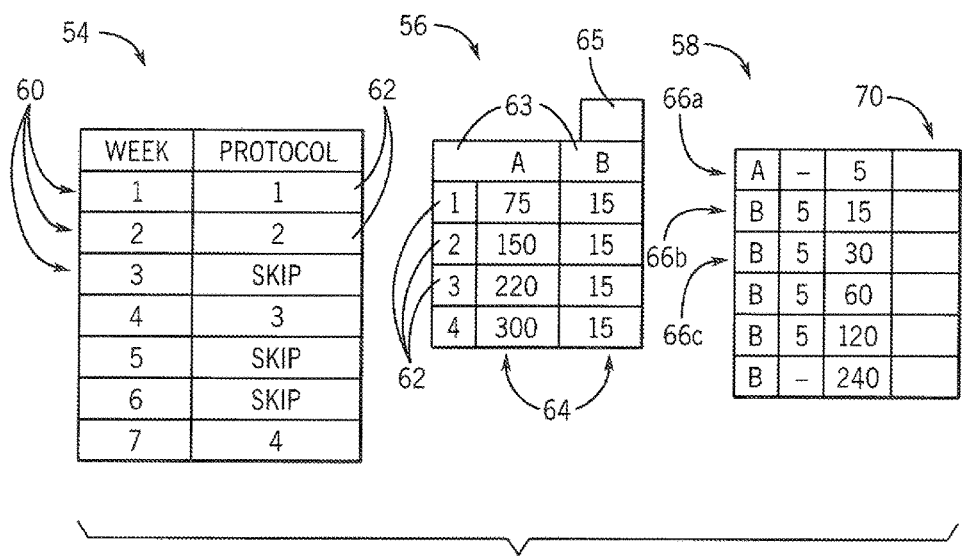
FIG. 3 is a logical representation of a treatment schedule and session protocol including doses and protocol steps as stored electronically in the pump of FIGS. 1 and 2.
Figure 4:
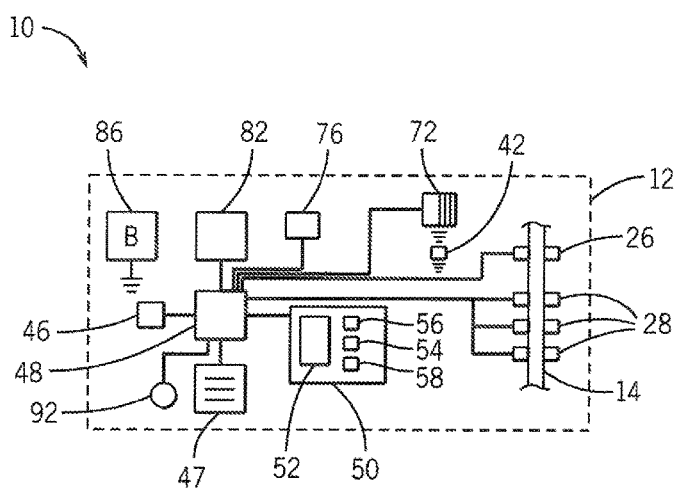
FIG. 4 is a schematic block diagram of the principal elements of the pump of FIGS. 1 and 2 employing a processor executing a program stored in memory for the control of a syringe pump and peristaltic infusion pump.

Referring now to FIGS. 3 and 4, the pump 10 may provide an internal processor 48 communicating with a non-volatile electronic memory 50. The electronic memory 50 may hold a stored operating program 52, a stored treatment schedule 54, and stored protocols each including protocol dose table 56 and protocol sequence instructions 58. Generally, the treatment schedule 54 will provide a set of treatment dates 60 each associated with a treatment session represented here as a row in a table. A given session (row) may be linked with a particular protocol (and hence a given row 62 in protocol dose table 56 and a different set of protocol sequence instructions 58) or an indication that treatment is skipped on that particular session. Normally there will be one session per day although multiple sessions per day are also possible. A session may be characterized by being separated from other sessions I. Time during which the pump 10 is disconnected from the patient and/or different drugs are different delivery protocols are used.

For each session of the treatment schedule 54, the protocol dose table 56 provides a row 62 giving doses 64 of different medicaments, for example, of medicament "A" and medicament "B" as part of a two-medicament treatment.

For each session of the treatment schedule 54, the steps of the protocol sequence instructions 58 will be implemented using the doses from the protocol dose table 56. One set of protocol sequence instructions 58 may be shared among all sessions or different sessions may have different protocol sequence instructions 58. The protocol sequence instructions 58 generally provide a total amount of medicament delivery and a rate of delivery of medicament for each medicament and provide sequence steps which define an order of medicament delivery. For example, in at first step 66a of the protocol sequence instructions 58, medicament A may be delivered until exhausted (indicated by the hyphen) at a flow rate of five millimeters per minute. The next step 66b may deliver medicament B for five minutes at a flow rate of 15 milliliters per minute, and a third step 66c may deliver medicament B for five minutes at a delivery rate of 30 milliliters per minute and so forth. Each step 66 may be associated with text instructions 70 which may be relayed to the patient through the display 47 and may require acknowledgment by the patient through pressing of the entry button 46. In this way the patient may be prompted through the various steps that the patient needs to assist with. The instructions delivered through the display 47 may also proceed the delivery of the medicaments to instruct the patient as to how to prepare and load the medicaments into the pump 10.

The protocol dose table 56 may also provide identification of the particular medicaments, for example, in field 63 which may be displayed through display 47. The protocol dose table 56 may also identify the patient for whom the protocols have been developed in field 65 which will be used for a patient confirmation process to be described below.

Referring to FIGS. 2 and 4, the processor 48 may communicate with a pump motor 72, for example, a stepper motor, communicating with the drive arm (shown in FIG. 2) that may press plunger 44 of the syringe 20 so that the protocol steps related to the syringe 20 may be implemented under control of the processor 48. In particular, the stepping speed of the motor 72 and the number of steps is controlled to provide both the desired flow rate and dose amount of medicament 22 in syringe 20.

Likewise the processor 48 may communicate with IV clamp elements 26 (shown in FIG. A) to prevent the flow of medicament 18, for example, from pooling bag 16 until completion of the delivery of medicament 22 in the syringe 20. Peristaltic pump reciprocating actuators 28 may also be controlled by the processor 48 which sequences them to alternately compress and release the IV line 14 to pump and meter (that is, control a delivery rate and amount) therethrough as required by the protocol.

Referring now to FIGS. 1 and 3, the processor 48 may also provide for a near field code sensor 76, for example, an RFID (radiofrequency identification) reader that may read an RFID tag 78 on either or both of the pooling bag 16 and the syringe 20 which may be used to confirm proper medicament when the medicaments are prepackaged in these delivery containers. Alternatively the tags 78 may be on secondary containers from which the medicaments are transferred into the pooling bag 16 and syringe 20 by the patient.

A similar RFID tag 78, for example, on a card 80 in the possession of the patient, may be used to confirm patient identity and/or dose to provide additional safety with patient implemented procedures.

In general, the RFID tag 78, may be replaced with any similar near field code sensing technology, such as a barcode reader, Bluetooth device, etc., implicitly indicating a physical proximity between the communicating devices such as at once indicates the identity and the location of the tag 78.

The processor 48 may also communicate with a wireless transmitter 82, for example, a cellular communication radio or Wi-Fi transceiver. The wireless transmitter 82 allows data to be received by the pump 10 for updating stored operating program 52 or changing the data of treatment schedule 54, protocol dose table 56, and protocol sequence instructions 58, for example, when the initially commissioning the pump 10 or for the purpose of changing features of the sessions and protocols when the patient consults with the patient's physician. The wireless transmitter 82 may also allow for reporting of status of the sessions for the purpose of patient compliance and safety monitoring.

The pump 10 may also provide a connection to line voltage or be battery-powered using battery 86 according to techniques known in the art.

Figure 5:
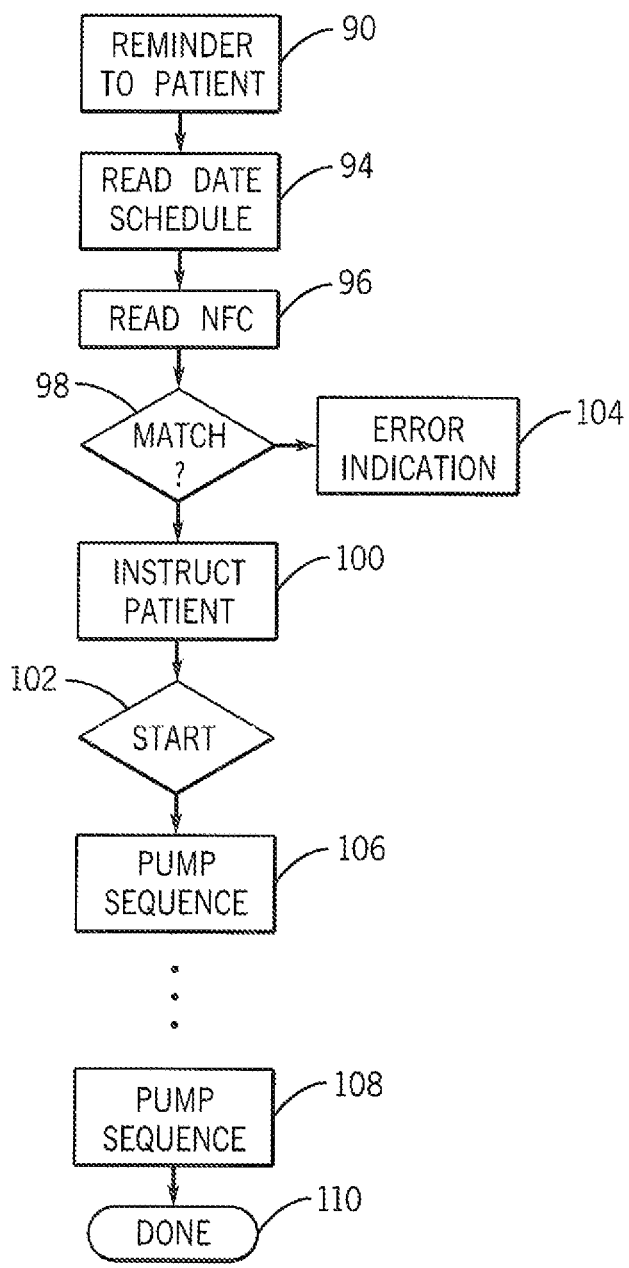
FIG. 5 is a flow-chart of the program executed by the pump in implementing the treatment schedule and protocols of FIG. 3.

Referring now to FIGS. 3 and 5, the program 52 in the pump, which has the ability to identify different sessions and execute the appropriate protocol when executed by the processor 48, may accordingly provide a reminder feature to the patient as indicated by process block 90 in which the program refers to the treatment schedule 54 and an internal clock calendar to remind the patient that a session is pending or due. This reminder may be via the display 47 or audio transducer 92, for example, a speaker or the like, providing tones or voice alerts at regular intervals during the day.

At these times, display 47 may provide instructions to the patient to press the button 46 to receive instructions for preparing for the upcoming session. In one embodiment these preparation include instructions where the patient confirms his or her identity, is given information about properly loading medicaments into the syringe 20 and pooling bag 16, and loading the syringe 20 and IV line 14 into the pump 10 as well as insertion of the needle 34.

During these preparatory instructions, as indicated by process block 94, the program may read the protocol dose table 56 and field 63 and may interrogate the installed drug containers using the near field code sensor 76 to confirm proper medicaments and container sizes have been installed as indicated at process block 96.

If there is a correct matching between the patient drugs and the drugs enrolled in protocol dose table 56, as determined at decision block 98, the program may instruct the patient to initiate the procedure per process block 100 to provide for the automatic execution of the therapy. At decision block 102, if the patient has pressed the enter button 46, the session may begin.

If at decision block 98 there is no matching between the patient and/or the drugs and the information in protocol dose table 56, an error is indicated at process block 104 which provides instructions to the patient, for example, to contact the patient's physician.

At decision block 102, once the process is initiated by the patient, the pump 10 may execute a protocol of protocol dose table 56 and protocol sequence instructions 58, pumping a sequence of medicament per process block 106 (per steps in protocol sequence instructions 58) followed by the pumping of medicament B per later steps in protocol sequence instructions 58) at process block 108. At any time during this pumping process, instructions may be provided to the patient to allow adjustment, for example, of pumping rate or to terminate the process using button 46 or 45.

When all of the steps of protocol sequence instructions 58 have been executed, the program concludes as indicated by process block 110 and instructions are provided to the patient, for example, for disassembly and cleaning of the equipment. The program then proceeds to process block 90 at the next scheduled session time.

Also at process block 110, a successful completion may be logged and transmitted, for example, to a remote system for the purpose of patient compliance recordation and/or to schedule additional drug deliveries or therapy associated checkups.

While the invention has been described with respect to an embodiment providing a syringe pump and a peristaltic infusion pump, it will be appreciated that a similar linkage of a portable pump to a particular therapeutic protocol employing two syringe pumps or two infusion pumps for protocols that require medicaments that favor one type of pump or the other are also possible. The embodiment of using one syringe pump and one peristaltic pump is for illustration purpose. The functions and features described could be realized by only one syringe pump, only one peristaltic pump, or pump with other pumping mechanisms.

At each of process blocks 90, 96, 100, 106, and 108, the pump 10 may provide instructions to the patient on display 47 indicating not only the state of the therapy but also steps that the patient must accomplish. The display 47 may also provide indications of the intended dose and flow rate for confirmation by the patient. Each of these instructions in the response by the patient may be stored in a log file that may be relayed to a healthcare professional, for example, to help the patient if they have trouble or questions with respect to any of the steps. The healthcare professional may review the log file to determine the steps completed and to provide guidance, for example, over the telephone or the like.

A metering device used herein indicates a device that can provide a quantitative delivery of an amount of fluid.

Certain terminology is used herein for purposes of reference only, and thus is not intended to be limiting. For example, terms such as "upper", "lower", "above", and "below" refer to directions in the drawings to which reference is made. Terms such as "front", "back", "rear", "bottom" and "side", describe the orientation of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second" and other such numerical terms referring to structures do not imply a sequence or order unless clearly indicated by the context.

When introducing elements or features of the present disclosure and the exemplary embodiments, the articles "a", "an", "the" and "said" are intended to mean that there are one or more of such elements or features. The terms "comprising", "including" and "having" are intended to be inclusive and mean that there may be additional elements or features other than those specifically noted. It is further to be understood that the method steps, processes, and operations described herein are not to be construed as necessarily requiring their performance in the particular order discussed or illustrated, unless specifically identified as an order of performance. It is also to be understood that additional or alternative steps may be employed.

References to "a microprocessor" and "a processor" or "the microprocessor" and "the processor," can be understood to include one or more microprocessors that can communicate in a stand-alone and/or a distributed environment(s), and can thus be configured to communicate via wired or wireless communications with other processors, where such one or more processor can be configured to operate on one or more processor-controlled devices that can be similar or different devices. Furthermore, references to memory, unless otherwise specified, can include one or more processor-readable and accessible memory elements and/or components that can be internal to the processor-controlled device, external to the processor-controlled device, and can be accessed via a wired or wireless network.

It is specifically intended that the present invention not be limited to the embodiments and illustrations contained herein and the claims should be understood to include modified forms of those embodiments including portions of the embodiments and combinations of elements of different embodiments as come within the scope of the following claims. All of the publications described herein, including patents and non-patent publications, are hereby incorporated herein by reference in their entireties.

We claim:

1. A programmable medical pump comprising:
a housing holding:
a first and second metering pump wherein
the first metering pump is a syringe pump for receiving and activating a plunger providing delivery of a predetermined first volume of a first medicament from a syringe holding a first medicament;
the second metering pump is a peristaltic pump for receiving and activating actuators controlling delivery of a predetermined second volume of a second medicament through an IV tube attached to a medicament container, the syringe volume being smaller than the medicament container volume;
a controller independently controlling the syringe pump to deliver a first predetermined volume of the first medicament at a first predetermined flow rate and the peristaltic pump to deliver a second predetermined volume of the second medicament at a second predetermined flow rate;
an electronic memory holding a multi-session treatment schedule spanning multiple days describing different treatment sessions and treatment protocols for a delivery of liquid medicament through the syringe pump and peristaltic pump for each session;
an interface display;
a start control; and
an electronic computer communicating with the interface display, start control, syringe pump and peristaltic pump, and an electronic memory executing a stored program fixed in a non-transitory medium to:
(1) identify a current session of the treatment schedule;
(2) provide an alert to a patient indicating the current session is due;
(3) determine a treatment protocol for the current session; and
(4) activate, via the start control, the treatment protocol controlling a sequential delivery of the first medicament at the first predetermined flow rate followed by the second medicament at the second predetermined flow rate for the current session for both the first and second metering pumps;

wherein the interface display communicates with the electronic computer and wherein the electronic computer executes the stored program to display, via the interface display, (i) a calendar to identify a particular session based on a calendar day of the session, (ii) step by step instructions relative to the treatment protocol requiring user intervention, and (iii) a current session of the treatment protocol.

2. The programmable medical pump of claim 1 wherein the interface display displays the reminders.

3. The programmable medical pump of claim 1 wherein the interface display is selected from the group consisting of: a text display and an image display.

4. The programmable medical pump of claim 1 wherein the current session identifies at least one medicament for the protocol.

5. The programmable medical pump of claim 1 further including a reader reading the treatment protocol from a storage element proximate to the reader.

6. The programmable medical pump of claim 5 wherein the reader is a near field communication reader.

7. The programmable medical pump of claim 1 further including a wireless interface for communicating with a remote electronic device and wherein the electronic computer further communicates with the wireless interface to transfer data related to one of the multi-session treatment sessions.

8. The programmable medical pump of claim 7 wherein the electronic computer further communicates with the wireless interface to report successful completion of each session.

9. The programmable medical pump of claim 1 further including an interface for receiving input from a patient.

10. The programmable medical pump of claim 1 wherein the treatment protocols include amounts of medicine delivery for different sessions.

11. The programmable medical pump of claim 1 wherein the treatment protocols include a sequence of medicament deliveries using the syringe pump and peristaltic pump.

12. The programmable medical pump of claim 1 wherein the treatment protocols provide treatment ranges that may be modified by a patient during treatment.

13. The programmable medical pump of claim 1 further including a code sensor for reading encoded information on an identification device assessable by a patient to confirm the proper patient for the treatment sessions.

14. The programmable medical pump of claim 1 wherein the electronic computer determines that treatment is skipped for the current session.

15. The programmable medical pump of claim 1 wherein the first medicament and second medicament are delivered through a common IV tube.

* * * * *